(12) United States Patent
Arayama et al.

(10) Patent No.: US 9,889,050 B2
(45) Date of Patent: Feb. 13, 2018

(54) ABSORBENT ARTICLE

(71) Applicant: UNICHARM CORPORATION, Ehime (JP)

(72) Inventors: Takaya Arayama, Kagawa (JP); Hirotomo Mukai, Kagawa (JP)

(73) Assignee: Unicharm Corporation, Ehime (JP)

( * ) Notice: Subject to any disclaimer, the term of this patent is extended or adjusted under 35 U.S.C. 154(b) by 678 days.

(21) Appl. No.: 14/395,033

(22) PCT Filed: Apr. 19, 2013

(86) PCT No.: PCT/JP2013/061660
§ 371 (c)(1),
(2) Date: Oct. 16, 2014

(87) PCT Pub. No.: WO2013/161715
PCT Pub. Date: Oct. 31, 2013

(65) Prior Publication Data
US 2015/0105742 A1    Apr. 16, 2015

(30) Foreign Application Priority Data

Apr. 23, 2012 (JP) ................................. 2012-098248

(51) Int. Cl.
*A61F 13/496* (2006.01)
*A61F 13/49* (2006.01)
(Continued)

(52) U.S. Cl.
CPC .. *A61F 13/49011* (2013.01); *A61F 13/49001* (2013.01); *A61F 13/515* (2013.01);
(Continued)

(58) Field of Classification Search
CPC ............ A61F 13/49058; A61F 13/4906; A61F 13/49061; A61F 13/49063;
(Continued)

(56) References Cited

U.S. PATENT DOCUMENTS

2001/0007936 A1*  7/2001  Shimoe ............. A61F 13/49019
                                                    604/385.24
2002/0147438 A1* 10/2002  Tanaka .................. A61F 13/496
                                                    604/392

(Continued)

FOREIGN PATENT DOCUMENTS

CN         101547669 A     9/2009
CN         102368989 A     3/2012
(Continued)

OTHER PUBLICATIONS

International Search Report from corresponding PCT application No. PCT/JP2013/061660 dated Jul. 16, 2013 (8 pgs).
(Continued)

*Primary Examiner* — Susan Su
(74) *Attorney, Agent, or Firm* — Brinks Gilson & Lione

(57) ABSTRACT

An absorbent article that has an absorber which is disposed in the crotch region and an absorber backsheet which is positioned at the outer direction side of the absorber. At least either one of a front end of the absorber and a rear end of the absorber is disposed in the crotch region. In the front end of the absorber backsheet and the rear end of the absorber backsheet, an end at a side at which the absorber is positioned in the crotch region is disposed outboard of the crotch region in the longitudinal direction.

8 Claims, 12 Drawing Sheets

(51) Int. Cl.
*A61F 13/535* (2006.01)
*A61F 13/515* (2006.01)
*A61F 13/15* (2006.01)

(52) U.S. Cl.
CPC .. *A61F 13/535* (2013.01); *A61F 2013/15552* (2013.01); *A61F 2013/5355* (2013.01)

(58) Field of Classification Search
CPC .......... A61F 13/49065; A61F 13/49066; A61F 13/49017; A61F 13/49019
See application file for complete search history.

(56) References Cited

U.S. PATENT DOCUMENTS

| | | | |
|---|---|---|---|
| 2003/0040732 A1* | 2/2003 | Ishikawa | A61F 13/49017 604/385.29 |
| 2003/0078556 A1* | 4/2003 | Sasaki | A61F 13/4942 604/385.25 |
| 2011/0066125 A1* | 3/2011 | Otsubo | A61F 13/495 604/378 |
| 2012/0302985 A1* | 11/2012 | Mukai | A61F 13/15593 604/385.24 |
| 2013/0184669 A1* | 7/2013 | Mishima | A61F 13/49011 604/385.3 |
| 2014/0163509 A1* | 6/2014 | Gassner | A61F 13/49061 604/385.16 |

FOREIGN PATENT DOCUMENTS

| | | |
|---|---|---|
| DE | 202011000820 U1 | 9/2011 |
| EP | 1 709 870 A1 | 10/2006 |
| EP | 2 258 326 A1 | 12/2010 |
| GB | 2 266 445 A | 11/1993 |
| JP | 2690870 B | 10/1996 |
| JP | H10-510733 A | 10/1998 |
| JP | 2002-159526 A | 6/2002 |
| JP | 2006-043067 A | 2/2006 |
| JP | 2007-029479 A | 2/2007 |
| JP | 2008-212278 A | 9/2008 |
| JP | 2011-517985 A | 6/2011 |
| WO | WO 2008/069279 A1 | 6/2008 |
| WO | WO 2010/113470 A1 | 10/2010 |
| WO | WO 2011/105108 A1 | 9/2011 |
| WO | WO 2011/105412 A1 | 9/2011 |

OTHER PUBLICATIONS

Japanese Office Action and English translation from corresponding Japanese application No. 2012-098248 dated Sep. 8, 2015 (6 pgs).
European extended Search Report from corresponding European application No. 13781036.2 dated Oct. 27, 2015 (7 pgs).
Chinese Office Action and English translation from corresponding Chinese application No. 201380021370.7 dated Mar. 18, 2016 (15 pgs).
European Office Action from corresponding European application No. 13781036.2 dated Apr. 25, 2016 (4 pgs).
Chinese Office Action and English translation from corresponding Chinese application No. 201380021370.7 dated Jun. 30, 2015 (8 pgs).

* cited by examiner

ABSORBENT ARTICLE

RELATED APPLICATION

This application is a 35 U.S.C. § 371 national phase filing of International Patent Application No. PCT/JP2013/061660, filed Apr. 19, 2013, through which and to which priority is claimed under 35 U.S.C. §119 to Japanese Patent Application No. 2012-098248, filed Apr. 23, 2012.

TECHNICAL FIELD

The present invention relates to an absorbent article such as a disposable diaper.

BACKGROUND ART

In order to improve a wearing comfort of a wearer various methods have been devised in absorbent articles. For example, in Patent Literature 1, there is disclosure of a disposable pants as an absorbent article having a waistline gather to be fitted to a waistline of the wearer, in which an end in a longitudinal direction of an absorption member is disposed at a crotch side (inside in the longitudinal direction) than the waistline gather.

The disposable pants described in Patent Literature 1 is structured to arrange an absorption member between a liquid-impermeable sheet and a liquid-permeable sheet, and at least the liquid-impermeable sheet and the absorption member are disposed at the crotch side than the waistline gather. The disposable pants described in Patent Literature 1 is a disposable diaper in which the absorption member and the liquid-impermeable sheet and the waistline gather are disposed so that the absorption member and the waistline gather do not overlap with each other, the liquid-impermeable sheet and the waistline gather do not overlap with each other, and which is high in ventilation property, and which is capable of improving the wearing comfort of the wearer, in comparison with a disposable pants in which the absorption member and the waistline gather overlap each other, and the liquid-impermeable sheet and the waistline gather overlap each other (refer to Patent Literature 1, Paragraph 0009, FIG. 1, and FIG. 2 or the like).

CITATION LIST

Patent Literature

[PTL 1]
the publication of Japanese Patent No. 2690870

SUMMARY OF INVENTION

However, the disposables pant described above has entailed the following problems.

A bodily liquid discharged from a wearer is absorbed by an absorption member disposed so as to come into contact with a crotch of the wearer. In a case where a large amount of bodily liquid is discharged, there may be a case in which the bodily liquid disperses in a longitudinal direction or in a widthwise direction from the absorption member that is disposed so as to come into contact with the crotch and then the bodily liquid arrives in a region in which a waistline gather is disposed.

In so far as the disposable pants of Patent Literature 1 is concerned, since the absorption member and the liquid-impermeable sheet are disposed at the crotch side than the waistline gather, in case that bodily liquid disperses to the waistline gather side while exceeding the absorption member, it may be impossible to prevent a leakage of the bodily liquid by the liquid-impermeable sheet. Therefore, the leakage of the bodily liquid arises and conversely the wearing comfort of the wearer might be impaired.

Accordingly, it is an object of the present invention to provide an absorbent article which improves a ventilation property while preventing a leakage of bodily liquid, and which is capable of improving a wearing comfort of a wearer.

An absorbent article having: a longitudinal direction (longitudinal direction L) extending to a body front side and a body rear side of a wearer; a widthwise direction (widthwise direction W) perpendicular to the longitudinal direction; an inner direction (inner direction IN) for facing a wearer; an outer direction (outer direction OUT) which is opposite to the inner direction, a crotch region (crotch region S3) which is adapted to be in contact with a crotch of the wearer; a front waistline region (front waistline region S1) which is disposed forward of the crotch region, and is adapted to be in contact with a waistline of the wearer; a rear waistline region (rear waistline region S3) which is disposed rearward of the crotch region, and is adapted to be in contact with the waistline of the wearer, an absorber (absorber 40) which is disposed in the crotch region; and a liquid-impermeable sheet (absorber backsheet 30) which is positioned at the outer direction side of the absorber, wherein at least either one of a front end of the absorber and a rear end of the absorber is disposed in the crotch region, and in the front end of the liquid-impermeable sheet and the rear end of the liquid-impermeable sheet, an end at a side at which the absorber is positioned in the crotch region is disposed outboard of the crotch region in the longitudinal direction.

DESCRIPTION OF EMBODIMENTS

Figure 1:
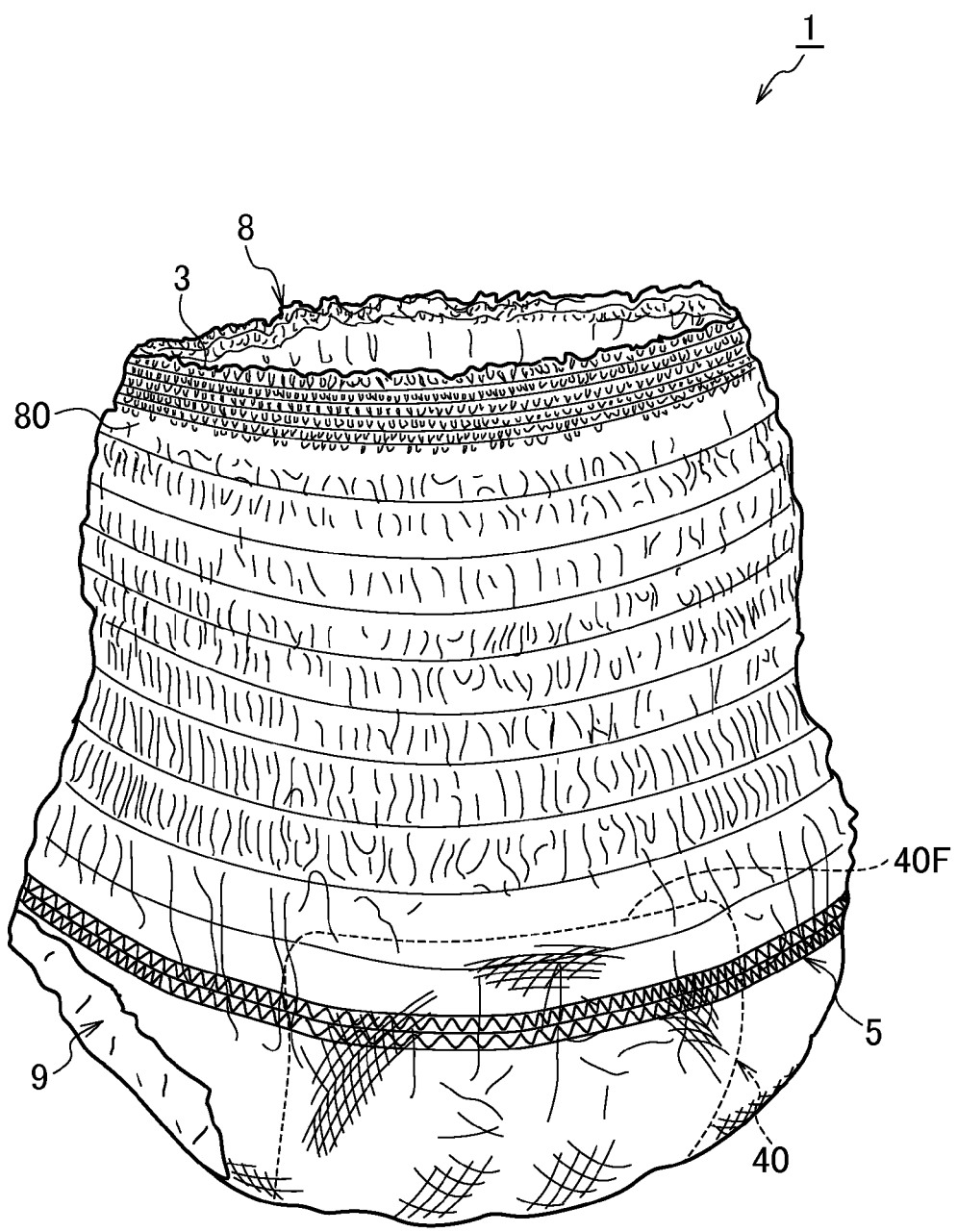
FIG. 1 is a schematic perspective view of a disposable diaper according to at least one embodiment.

Next, embodiments of a disposable diaper 1 as an absorbent article according to the present disclosure will be described with reference to the drawings. It is to be noted that in the following description of the drawings, same or similar constituent elements are designated by same or similar reference numerals. However, it should be kept in mind that the drawings are schematic representations and are not drawn to scale unless otherwise specified. Moreover, the drawings do not necessarily reflect the actual dimensional relationships and ratios of component. Therefore, specific dimensions or the like should be determined in consideration of the following description. In addition, relations or ratios among such dimensions may be different from one drawing to another.

The disposable diaper according to the embodiment is characterized in that a rear end of an absorber is disposed in a crotch region, a liquid-impermeable absorber backsheet is disposed on a non-skin contact side of the absorber, and a rear end of the absorber backsheet is disposed in a rear waistline region.

(1) Overall Schematic Configuration of the Disposable Diaper

Figure 2:
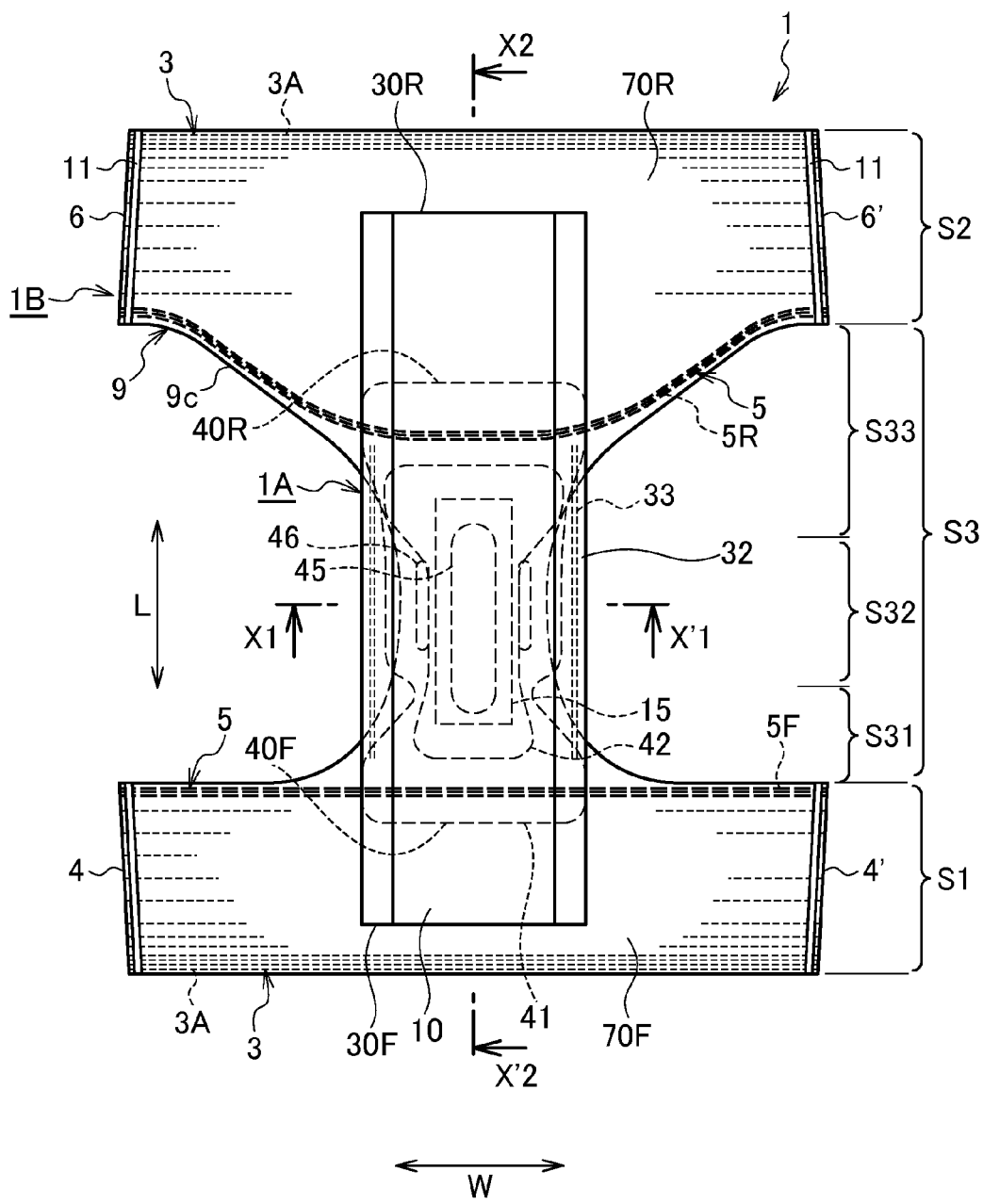
FIG. 2 is an exploded plan view of the disposable diaper according to at least one embodiment.
Figure 3:
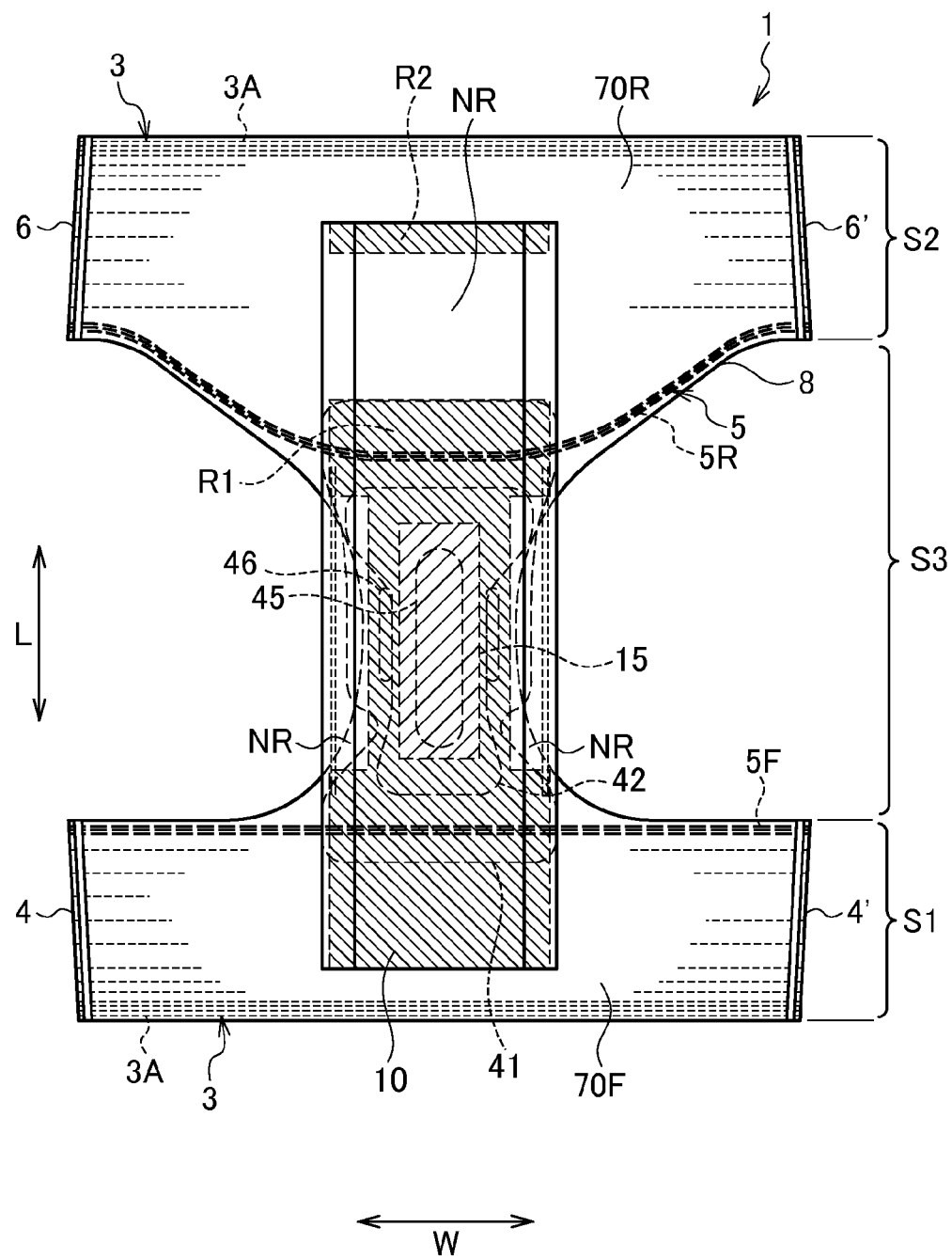
FIG. 3 is an exploded plan view of the disposable diaper according to at least one embodiment.
Figure 4:
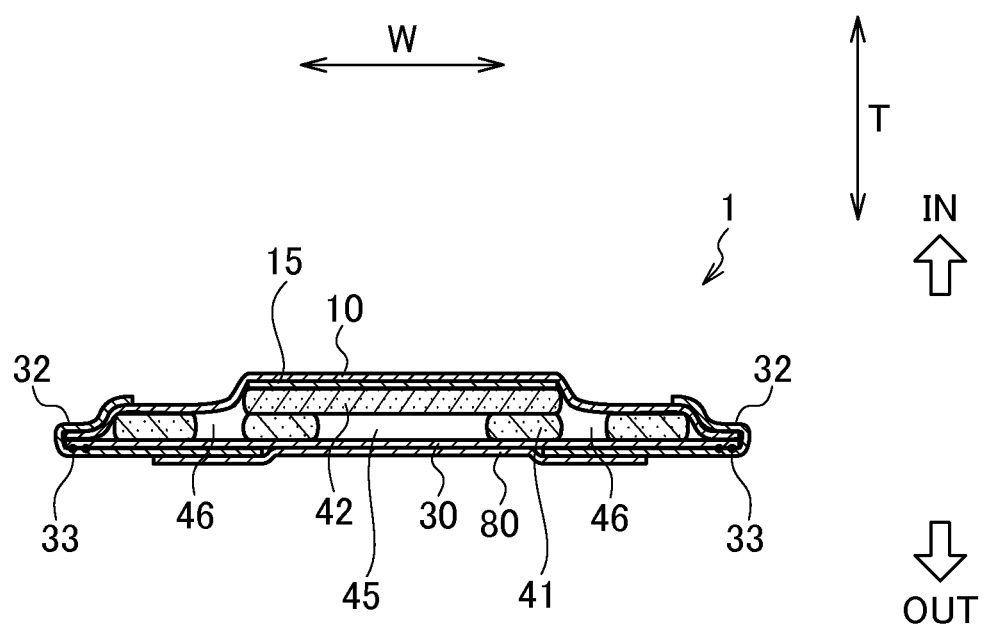
FIG. 4 is a cross-sectional view in the widthwise direction of the disposable diaper along the X1-X'1 line shown in FIG. 2.
Figure 5:
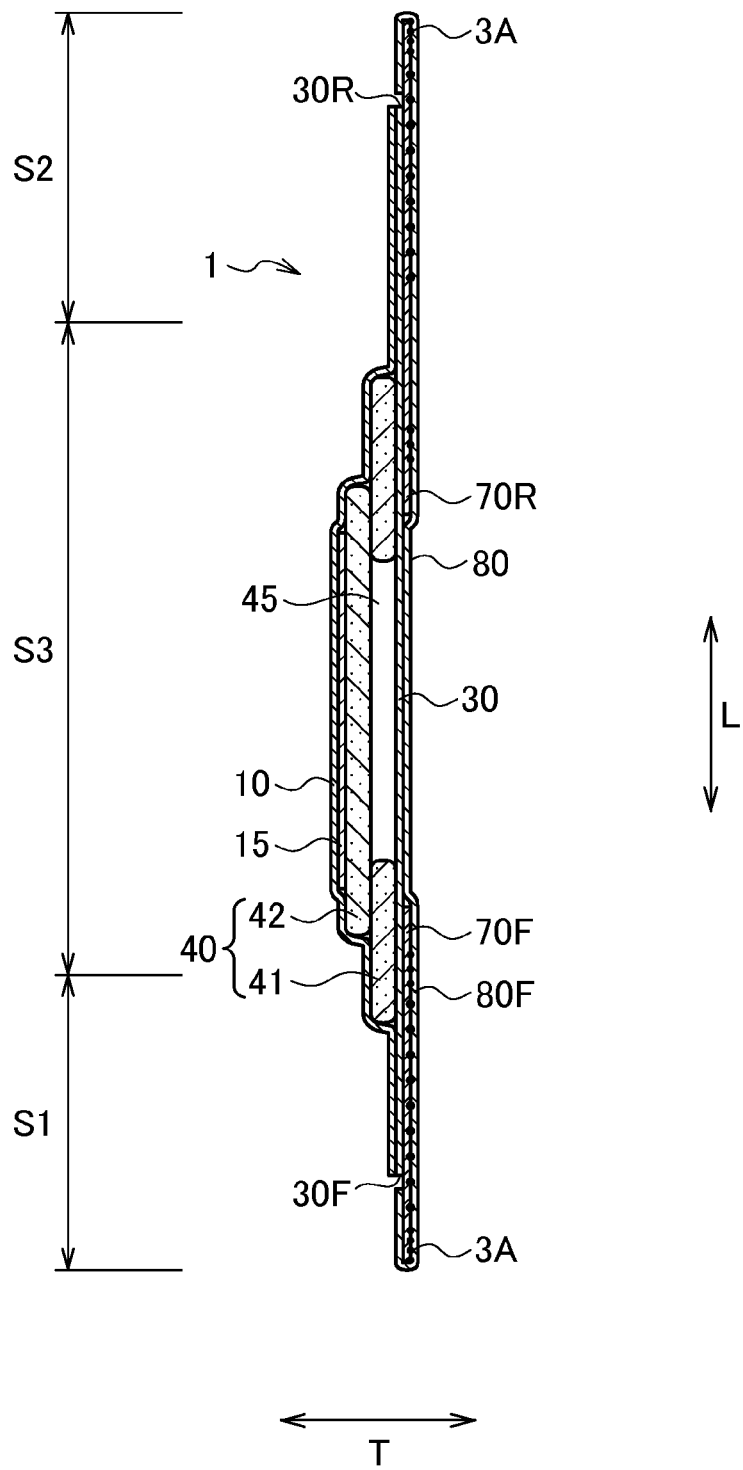
FIG. 5 is a cross-sectional view in the longitudinal direction of the disposable diaper along the X2-X'2 line shown in FIG. 2.

FIG. 1 is a perspective schematic view of a disposable diaper 1 that configures the disposable diaper in present embodiment. FIG. 2 and FIG. 3 are an exploded plan view of the disposable diaper 1 according to at least one embodiment. FIG. 4 is a cross-sectional view in the widthwise direction of the disposable diaper along the X1-X'1 line shown in FIG. 2. FIG. 5 is a cross-sectional view in the longitudinal direction of the disposable diaper along the X2-X'2 line shown in FIG. 2. The disposable diaper 1 is a pants-type disposable diaper.

A disposable diaper 1 has: a longitudinal direction L extending to a body front side and a body rear side of a wearer; a widthwise direction W perpendicular to the longitudinal direction; and a thickness direction T having an inner direction IN for facing a wearer and an outer direction OUT which is opposite to the inner direction.

The disposable diaper 1, as shown in FIG. 2, has, in a longitudinal direction L of the disposable diaper 1, a front waistline region S1 which is adapted to be in contact with a waistline of the wearer, a rear waistline region S2 is adapted to be in contact with a waistline of the wearer, and a crotch region S3 which is adapted to be in contact with a crotch of the wearer, and is positioned between the front waistline region S1 and the rear waistline region S2.

The crotch region S3 has: a central crotch region S32 which is the smallest in width when the legs are closed at the crotch of the wearer; a front crotch region S31 which is disposed between the central crotch region S32 and the front waistline region S1; and a rear crotch region S33 which is disposed between the central crotch region S32 and the rear waistline region S2.

A front waistline side edge 4 which is disposed outside in one widthwise direction of the disposable diaper 1 in the front waistline region S1 is joined with a rear waistline side edge 6 which is disposed outside in one widthwise direction of the rear waistline region S2, and a front waistline side edge 4' which is disposed outside in the other widthwise direction is joined with a rear waistline side edge 6' which is positioned outside in the other widthwise direction, whereby the disposable diaper 1 is formed to be of pants type. In the front waistline region and the rear waistline region of the disposable diaper of the pants type, a joint unit 11 of which the respective edge parts are joined with each other is formed, and the crotch region S3 is a region inner side of the joint unit 11 in the longitudinal direction.

In the disposable diaper 1, as shown in FIG. 1, there are formed: a waistline opening unit 8 disposed so as to surround the wearer's waistline and a pair of leg hole opening unit 9 disposed so as to surround the wearer's leg in a state in which it is formed in the shape of a pant.

The disposable diaper 1 includes: an absorbent main body 1A including a topsheet 10, an absorber 40, and an absorber backsheet 30 or the like; and an exterior body 1B including a foreside exterior topsheet 70F, a rear-side exterior topsheet 70R, and an exterior backsheet 80 or the like, and these constituent elements are joined to each other by an adhesive or thermal fusion bonding or the like.

The exterior body 1B includes: a foreside exterior topsheet 70F, a rear-side exterior topsheet 70R, an exterior backsheet 80, and constitutes an exterior portion of the disposable diaper 1. The foreside exterior topsheet 70F is disposed across the front waistline region S1 and the front crotch region S31. The rear-side exterior topsheet 70R is disposed across the rear waistline region S2 and the rear crotch region S33. The foreside exterior topsheet 70F and the rearside exterior topsheet 70R are spaced from each other in the longitudinal direction, and are disposed in the thickness direction between the exterior backsheet 80 and the absorbent main body 1A.

The foreside exterior topsheet 70F and the rear-side exterior topsheet 70R can be formed by an air-through nonwoven cloth, a spun bond nonwoven cloth, a SMS nonwoven cloth, or a water-resistive film. The foreside exterior topsheet 70F and the rear-side exterior topsheet 70R according to at least one embodiment are constituted of an SMS nonwoven cloth having a basis weight of 15 g/m2 of polypropylene.

The exterior backsheet 80 lies outside when the disposable diaper is worn. Namely, the exterior backsheet is disposed on a side on which they are spaced from the wearer's skin. The exterior backsheet 80 is disposed across the front waistline region S1 and the rear waistline region S2. Ends of the exterior backsheet 80 in longitudinal direction are folded back to the skin-contact face side, and are disposed so as to envelope an end in longitudinal direction of the foreside exterior topsheet 70F (or the rear-side exterior topsheet 70R).

The exterior backsheet 80 can be formed by an air-through nonwoven cloth, a spun bond nonwoven cloth, a SMS nonwoven cloth, or a water-resistive film. The exterior backsheet 80 according to at least one embodiment is constituted of a spun bond nonwoven having a basis weight of 17 g/m2 of polypropylene.

The absorbent main body 1A includes a topsheet 10, an auxiliary sheet 15, an absorber backsheet, and a leakage preventing unit, and is disposed is provided closer to the skin contact surface than the exterior body 1B.

The topsheet 10 is a sheet that forms the skin contact surface that can be in direct contact with the skin of the wearer. The topsheet 10 is provided closer to the skin contact surface than the absorber 40. The topsheet 10 is formed by a liquid-permeable sheet, such as a hydrophilic nonwoven cloth and a hydrophilic woven cloth, an aperture plastic film, or an aperture hydrophobic nonwoven cloth. The topsheet 10 according to at least one embodiment is formed of a hydrophilic point bond nonwoven cloth having a basis weight of 23 g/m2 of polypropylene.

An auxiliary sheet 15 is joined with the non-skin contact surface side of the topsheet 10. The auxiliary sheet 15 is disposed between the topsheet 10 and the absorber 40. Providing the auxiliary sheet 15 makes it possible to increase the speed at which the bodily fluid is absorbed, and makes it possible to prevent reversal of the bodily fluid after absorption.

The topsheet 10 and the auxiliary sheet 15 according to at least one embodiment are joined by adhesive. The auxiliary sheet 15 is made of, for example, an air-through nonwoven cloth, an aperture film, or the like. The auxiliary sheet 15 according to at least one embodiment is formed of air-through nonwoven cloth (hydrophilic) having a basis weight of 30 g/m2.

The absorber 40 is joined between a composite sheet on which the topsheet 10 and the auxiliary sheet 15 are joined with each other and the absorber backsheet 30 by a hot melt adhesive. The hot melt adhesive is respectively applied to the composite sheet and the backsheet, and is applied at a respective one of the basis weights of 5 g/m2 and 8 g/m2 by a spiral coating method, for example.

The rear end 40R of the absorber 40 is disposed in the crotch region S3, and the front end 40F of the absorber 40 is disposed in the front waistline region S1. At least either one of the front end 40F and the rear end 40R is disposed in the crotch region, whereby a ventilation property is improved, and a wearing comfort of a wearer can be improved, in comparison with a mode in which the absorber 40 extends to the front waistline region S1 and the rear waistline region S2.

The front waistline region and the rear waistline region come into intimate contact with the waistline of the wearer. By improving the ventilation property in the front waistline region and the rear waistline region, the ventilation property of the waistline of the wearer is improved, and the wearing comfort of the wearer can be improved.

Also, the front waistline region S1 is a region with which a man's urine opening comes into contact, and in which a large amount of bodily liquid is to be discharged. The front end 40F of the absorber 40 is disposed in the front waistline region S1 while exceeding the crotch region S3, whereby even if a large amount of bodily liquid is discharged, it is possible to absorb the bodily liquid and restrain the leakage. In particular, in so far as diapers for adult male or babies are concerned, since the leakage from the crotch region to the front waistline region is prone to easily arise, the disposable diaper according to the embodiment can be preferably employed.

In addition, since a length in the longitudinal direction of the absorber is small in comparison with a mode in which both of the front end and the rear end of the absorber are disposed in the front waistline region and the rear waistline region, a total weight of pulp can be reduced while a basis weight of the pulp of the absorber is maintained. By reducing the total weight of pulp while maintaining the basis weight of the pulp, materials costs can be reduced without degrading an absorption speed of bodily liquid.

Incidentally, it is sufficient if at least either one of the front end 40F and the rear end 40R of the absorber 40 is disposed in the crotch region S3. For example, both the front end and the rear end of the absorber 40 may be disposed in the crotch region, or alternatively, it may be that the rear end of the absorber 40 is disposed in the crotch region, and the front end of the absorber is disposed in the front waistline region.

The absorber 40 is formed of a mixed powder of ground pulp, highly absorbent polymer, and the like. The absorber 40 is configured using a first absorbent layer 41 disposed at the non-skin contact surface side of the wearer and a second absorbent layer 42 overlapping with the first absorbent layer 41 and disposed at the skin contact surface side of the wearer (see FIG. 7).

The first absorbent layer 41 has a central slit 45 constituting a central curving unit and side slit 46 constituting side curving units. The central slit 45 formed in the center of the first absorbent layer in the widthwise direction. A pair of side slits 46 is formed outboard of the central slit 45 in the widthwise direction. This diaper is constituted with central slit and side slits or the like formed on the absorber 40 so that the absorber 40 is curved when the disposable diaper 1 is worn. It is to be noted that a structure of the absorber will be described later in detail.

The absorber backsheet 30 is provided at a non-skin contact surface side of the absorber 40. The absorber backsheet 30 is formed of a sheet such as a liquid-impermeable film (for example, polyethylene).

The absorber backsheet 30 is disposed in an outer direction OUT more significantly than the absorber, and is formed of a liquid non-permeable. The absorber backsheet 30 is disposed so as to be extensive to the outside in the longitudinal direction more significantly than the absorber 40.

The rear end 30R of the absorber backsheet 30 is disposed more rearward than the rear end 40R of the absorber 40 and is disposed in the rear waistline region S2. Also, the front end 30F of the absorber backsheet 30 is disposed more forward of the front end 40F of the absorber 40 and is disposed in the front waistline region S1.

In so far as the front end 30F and the rear end 30R of the absorber backsheet 30 are concerned, it is sufficient if at least an end (the rear end 30R in the embodiment) at a side at which the absorber is positioned in the crotch region be disposed to be outside in the longitudinal direction more significantly than the crotch region. Therefore, in the embodiment, it may be that the rear end 30R of the absorber backsheet 30 is disposed in the rear waistline region, and the front end 30F of the absorber backsheet 30 is disposed in the crotch region.

For example, in a mode in which the front end of the absorber is disposed in the crotch region, it may be that the rear end 30R of the absorber backsheet 30 is disposed in the crotch region, and the front end 30F of the absorber backsheet 30 is disposed in the front waistline region, or alternatively, it may be that the rear end 30R of the absorber backsheet 30 is disposed in the rear end, and the front end 30F of the absorber backsheet 30 is disposed in the front waistline region.

Figure 6:
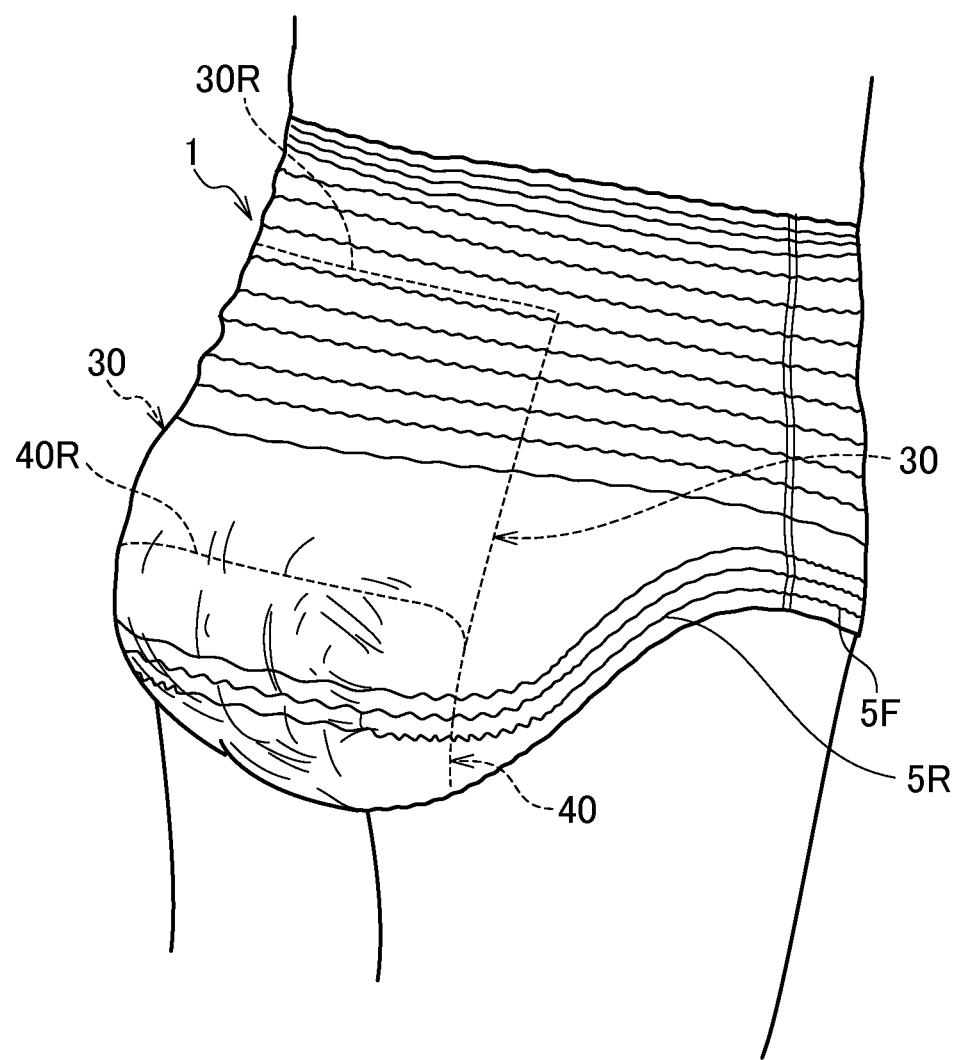
FIG. 6 is a schematic perspective view that schematically illustrates the wearing state of the disposable diaper 1 according to at least one embodiment.

FIG. 6 is a perspective rear view schematically depicting a state in which a disposable diaper according to an embodiment is worn. The rear end 40R of the absorber 40 is disposed at the crotch region S3 side more significantly than the rear waistline region S2, and the absorber 40 is disposed so as not to cover the entire buttocks of a wearer. Therefore, the ventilation property of the rear waistline region can be improved. On the other hand, the rear end 30R of the absorber backsheet 30 is disposed in the rear waistline region while extending more rearward than the rear end 40R of the absorber 40, and is disposed so as to cover the buttocks.

At one of the front end and the back end of the absorber (at an end disposed in the crotch region), the absorber backsheet extends up to the front waistline region or the rear waistline region while exceeding the crotch region, whereby even in the case bodily liquid disperses in the longitudinal direction, the leakage of bodily liquid can be prevented by the absorber backsheet. Therefore, even if the length of the absorber is reduced, permeation of the bodily liquid having dispersed while exceeding the absorber into an exterior body 1B can be prevented by the absorber backsheet. Accordingly, the ventilation property is improved while the leakage of bodily liquid is prevented, and the wearing comfort of the wearer can be improved.

The leakage preventing unit has a leakage preventing side sheet 32 and a leakage preventing elastic member 33, and is disposed along the longitudinal direction at a widthwise end of the absorber 40. The leakage preventing side sheet 32 is provided so as to integrally envelope the topsheet 10 and the absorber backsheet 30 at both side ends in the widthwise direction W of the absorber 40.

The leakage preventing side sheet 32 is formed of a sheet such as a liquid impermeable nonwoven cloth. One end of the leakage preventing side sheet 32 in the widthwise direction is joined with a non-skin surface of the absorber backsheet 30, and the other end in the widthwise direction of the leakage preventing side sheet 32 is folded back from a lateral of absorber in widthwise direction to the top sheet side, and is joined with a face of the skin contact face side of the topsheet 10.

The leakage preventing side sheet 32 is joined with the topsheet or the like by a hot melt adhesive. In the embodiment, a plurality of hot melt adhesives was applied in basis weight of 0.1 g/m2 by bead coating method. In addition, the leakage preventing side sheet 32 is constituted with a sheet of a hydrophobic nonwoven cloth, and in the embodiment, the leakage preventing side sheet 32 is constituted with an SMS nonwoven cloth having a basis weight of 15 g/m2 of polypropylene.

The leakage preventing elastic member 33 is adhered between the absorber backsheet 30 and the leakage preventing side sheet 32 in an expanded state. A hot melt adhesive can be exemplified as a means for bonding the leakage preventing elastic member. In the embodiment, Spandex is employed as the leakage preventing elastic member 33, and is directly applied by V slot method. More specifically, three leakage preventing elastic members 33 are each expanded and fixed with a thickness of 780 dtex and an expansion magnification of 2.3 times.

The leakage preventing elastic members 33 are disposed so as to substantially communicate with a leg gather to be described later in a planar view. Thus, the leakage preventing elastic members and the leg gather are disposed, whereby there can be attained advantageous effects that the wearer's leg feed can be tightened so as to be surrounded, a fitting feeling of leg feed is improved, and displacement or leakage of the disposable diaper is prevented.

The absorbent main body 1A and the exterior body 1B thus structured are partially bonded with each other by hot melt adhesive or the like. An adhesive region in which the absorbent main body 1A and the exterior body 1B are bonded with each other is indicated by the dashed line in FIG. 3. The adhesive region, in a planar view, has: a first adhesive region R1 which is positioned in a region in which an absorber is disposed; and a second adhesive region R2 which is positioned in the vicinity of a rear end of the absorber backsheet 30.

The first adhesive region R1 is provided in a region excluding the outside in a widthwise direction at a center in a longitudinal direction in the region in which the absorber 40 is disposed. A front end of the first adhesive region R1 is coincident with the front end 30F of the absorber backsheet 30, and a rear end of the first adhesive region R1 is coincident with the rear end 40R of the absorber 40.

In the region in which the absorber 40 is disposed, outside in the widthwise direction at the center of the longitudinal direction, there is provided a non-adhesive region NR in which the absorbent main body 1A and the exterior body 1B are not bonded with each other. The non-adhesive region is thus provided, whereby it is difficult for the exterior body 1B to inhibit deformation of the absorber exerted by a side curving unit which will be described later. Further, even in the case where a crotch width of the absorbent main body 1A is reduced by the deformation of the absorbent, the exterior body 1B can be disposed so as to cover a wearer's skin, and an uneasy feeling of a leakage of bodily liquid can be reduced.

The second adhesive region R2 is a region in which the absorber backsheet 30 and a rear-side exterior topsheet 70R are bonded with each other in the vicinity of a rear end of the absorber backsheet 30. A rear end of the second adhesive region R2 is coincident with the rear end 30R of the absorber backsheet 30.

The first adhesive region R1 and the second adhesive region R2 are spaced from each other in the longitudinal direction. Between the first adhesive region R1 and the second adhesive region R2, there is provided a non-adhesive region NR in which the absorbent main body 1A and the exterior body 1B are not bonded with each other. The non-adhesive region NR is provided more rearward than the rear end 40R of the absorber 40.

The first adhesive region R1 and the second adhesive region R2 are a region in which an adhesive such as a hot melt adhesive applied, and in general, a region in which an adhesive is applied is lowered in ventilation more significantly than a region in which no adhesive is applied. Therefore, between the first adhesive region R1 and the second adhesive region R2, there is provided the non-adhesive region NR in which no adhesive is applied, whereby the ventilation property of the exterior body 1B can be ensured while an occurrence of wrinkle or folding of the absorber 40 is prevented.

In particular, the disposable diaper 1 according to the embodiment is structured so that the rear end 40R of the absorber 40 is disposed in the crotch region S3, and the ventilation property at the rear side of the absorber 40 is improved. By providing the non-adhesive region NR rearward of the absorber 40, the ventilation property is further enhanced, and the wearing comfort of the wearer can be improved.

A waist gather 3 is provided in the front waistline region S1 and the rear waistline region S2. The waist gather 3 has an elongated waist elastic member 3A, such as a synthetic rubber, which is arranged so as to expand and contract along the widthwise direction W of the absorber 40. The waist gather 3 is continuous from one front waistline side edge 4 lying outside in the widthwise direction W of the disposable diaper 1 in the front waistline region S1 up to the other front waistline side edge 4' and is continuous from one rear waistline side edge 6 lying outside in the widthwise direction W of the disposable diaper 1 in the rear waistline region S2 up to the rear waistline side edge 6'.

A leg gather 5 is provided around leg opening unit 9.

The leg opening unit 9 is structured so as to be disposed along a leg-line of a wearer. The leg opening unit 9 is also structured so as to have an inclination part 9C toward the outside in the widthwise direction as it goes from the center in the longitudinal direction of the crotch region to the outside in the longitudinal direction. The inclination part is formed in a curved shape in a planar view.

It is to be noted that the leg opening unit 9 may be formed in a curved shape in a planar view, may be formed in a linear shape in a planar view, or alternatively, may be structured by using a combination of the curved shape and the linear shape At least a part of the leg gather 5 is disposed along the leg opening unit 9. The leg gather 5 is formed of: a front leg-holes elastic member 5F which is disposed in the front waistline region S1; and a rear leg-holes elastic member 5R which is disposed across the rear waistline region S2 and the crotch region S3.

The leg-holes elastic member 5R is disposed from the rear waistline region S2 to the crotch region S3, and is disposed toward the inside in the widthwise direction as it goes from the rear waistline region S2 to the crotch region S3. The rear leg-holes elastic member 5R in a region outside in the widthwise direction more significantly than the absorber functions to bring the leg opening unit 9 into intimate contact with the leg-line of the wearer, and the rear leg-holes elastic member 5R in a region overlapping the absorber functions to pull up the absorber to the wearer's side.

The front leg-holes elastic member 5F is disposed along the widthwise direction in the front leg-line region S1. The front leg-holes elastic member 5F in the region outside in the widthwise direction more significantly than the absorber functions to bring the leg opening unit into intimate contact with the leg-line of the wearer, and the front leg-holes elastic member 5F in a region overlapping the absorber functions to pull up the absorber to the wearer's side.

The front leg-holes elastic member 5F is disposed between the foreside exterior topsheet 70F and the exterior backsheet 80, and the rear leg-holes elastic member 5R is disposed between the rear-side exterior topsheet 70R and the exterior backsheet 80. Also, the waist elastic member 3A The waist elastic member 3A, the front leg-holes elastic member 5F, and the rear leg-holes elastic member 5R are fixed to the foreside exterior topsheet 70F or the rear-side exterior topsheet 70R and the exterior backsheet by adhesive (for example, by a hot melt adhesive) in an expanded state. In the embodiment, in so far as the waist elastic member 3A is concerned, a hot melt adhesive is applied to the topsheet side in a V-slot approach, and in so far as the front leg-holes elastic member 5F and the rear leg-holes elastic member 5R respectively are concerned, a hot melt adhesive is applied to the backsheet side in a control seam approach.

The waist elastic member 3A, the front leg-holes elastic member 5F, and the rear leg-holes elastic member 5R are composed of spandex. Six waist elastic members 3A each are fixed to be expanded in thickness of 940 dtex and at an expansion magnification of 3.5 times in the vicinity of the waistline opening unit 8, and the eight waist elastic members each are fixed to be expanded in longitudinal manner in thickness of 780 dtex and at an expansion magnification of 3.0 times inside in the longitudinal direction more significantly than the six elastic member. Three front leg-hole elastic members 5F and three rear leg-holes elastic members 5R each are fixed to be expanded in thickness of 780 dtex and at an expansion magnification of 1.5 times to 3.5 times. It is to be noted that the thicknesses, the expansion magnifications, and the numbers of waist elastic members 3A, front leg-holes elastic members 5F, and rear leg-holes elastic members 5R can be variously set without being limitative thereto.

As a method for manufacturing the absorbent article thus structured, for example, the absorbent article can be manufactured by a method including the steps of: molding a first absorbent layer of an absorber; molding a second absorbent layer of the absorber; jointing the first absorbent layer and the second absorbent layer with each other; conveying the absorber or the like by a belt conveyor or the like; and bonding the conveyed absorber with a sheet material such as a topsheet in the course of conveyance. It is to be noted that other steps may be those in which manufacturing can be carried out in accordance with a publicly known manufacturing method.

Also, in the case where central slits or a side slits are provided in both of the first absorbent layer and the second absorbent layer, there may arise a displacement when the first absorbent layer and the second absorbent layer are overlapped with each other. For example, if a displacement arises in a widthwise direction, widths of one pair of side slits disposed at the left and right are reduced, a regular deformation cannot be made, an unbalanced absorber at the left and right is produced, and there is an apprehension that absorptivity or the wearing comfort is adversely affected. However, a central slit or a side slit is provided in either one of the first adsorption layer and the second absorbent layer, whereby a displacement of the side slit or the like can be prevented.

For each of the members that configure the disposable diaper 1 mentioned above, for example, the materials described in Japanese Unexamined Patent Application Publication No. 2006-346439 may be employed.

(2) Structure of the Absorber

Figure 7:
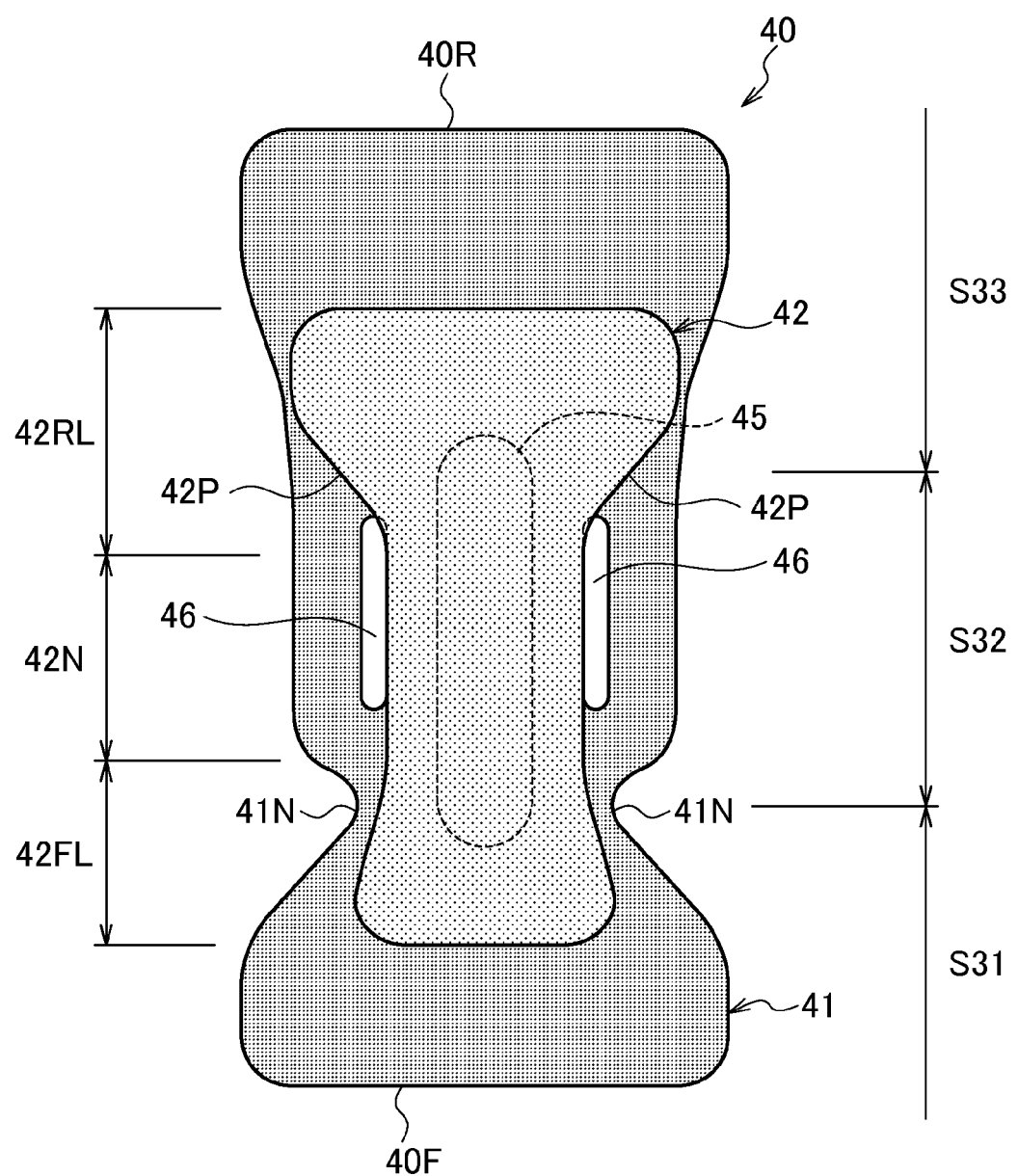
FIG. 7 is a plan view of an absorber according to at least one embodiment.
Figure 8:
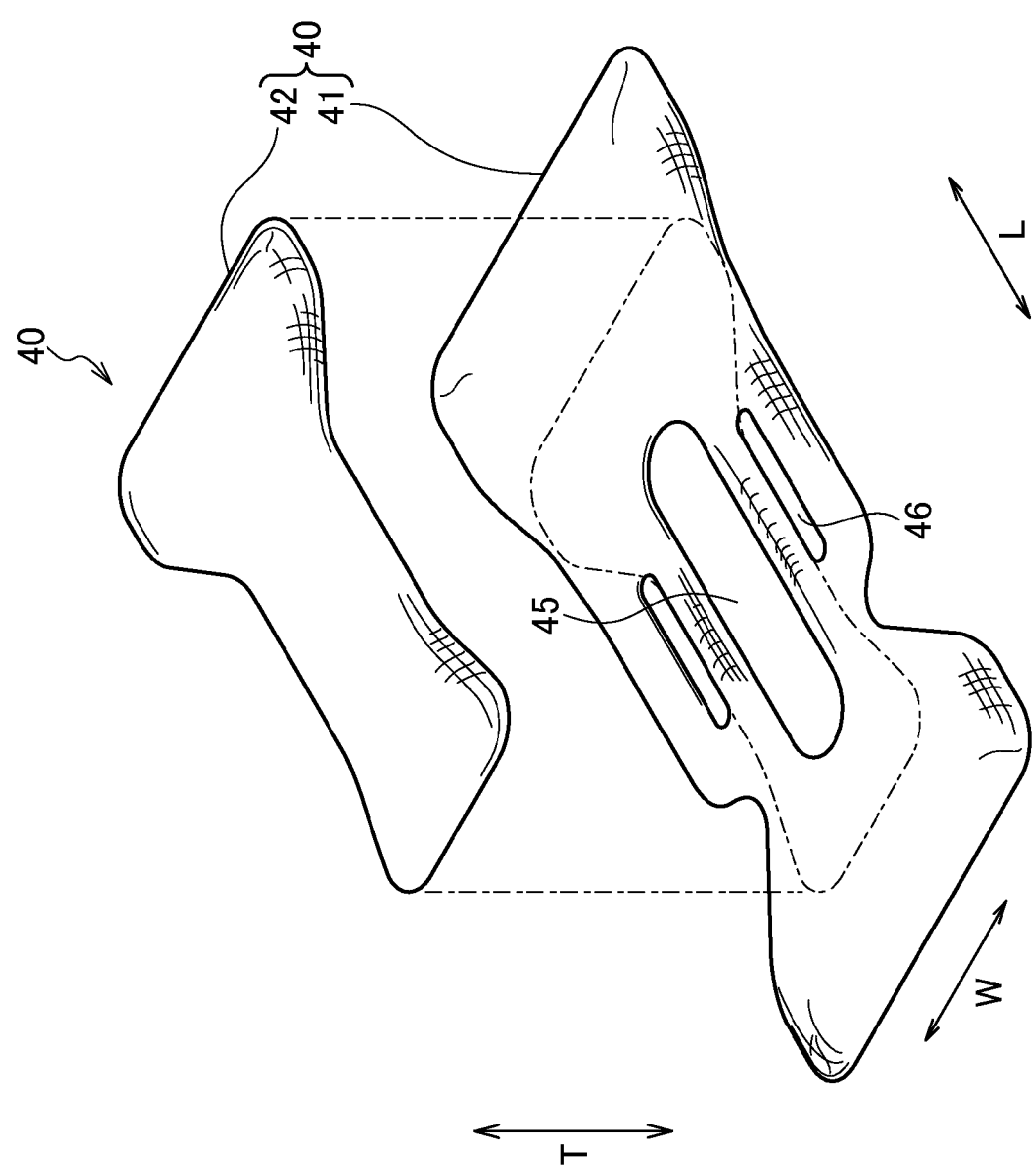
FIG. 8 is an exploded perspective view of an absorber according to at least one embodiment.

FIG. 7 is a plan view of the absorber 40. FIG. 8 is an exploded perspective view of an absorber according to at least one embodiment. As illustrated in FIG. 7 and FIG. 8, the absorber 40 has a first absorbent layer 41, and a second absorbent layer 42 positioned at the skin contact surface side than the first absorbent layer 41. The first absorbent layer 41 is positioned at the non-skin contact surface side of the wearer, and the second absorbent layer 42 is positioned at the skin contact surface side of the wearer.

The absorber 40 is disposed across the front waistline region S1 and the crotch region S3. A length in the longitudinal direction of the first absorbent layer 41 is greater than a length in the longitudinal direction of the second absorbent layer 42. The first absorbent layer 41 is disposed across the front waistline region S1 and crotch region S3, and the second absorbent layer 42 is disposed in the crotch region S3. A length in the widthwise direction of the first absorbent layer 41 is greater than a length in the widthwise direction of the second absorbent layer 42. The first absorbent layer 41 overhangs to the outer side in the widthwise direction more significantly than the second absorbent layer 42.

The first absorbent layer 41 and the second absorbent layer 42 are configured from cotton-like pulp and highly polymerized absorbent polymer (SAP). The absorber 40 can be formed by mixing, for example, 100 to 500 g/m2 pulp and 0 to 500 g/m2 SAP. The first absorbent layer 41 and the second absorbent layer 42 according to the present embodiment are formed from a mixture of 260 g/m2 pulp and 160 g/m2 SAP.

In the first absorbent layer 41, the central slit 45 and a pair of side slits 46 are formed. The central slit 45 has a longitudinally elongated shape extending along the longitudinal direction L, and is formed across the central crotch region S32, the front crotch region S31, and the rear crotch region S33. The central slit 45 is thus formed, whereby a central portion in the widthwise direction of the absorber can be easily curved in a convex manner in an inner direction IN which is the wearer's side. Also, the dispersion property of bodily liquid or the like in the longitudinal direction of the absorber is enhanced, the bodily liquid or the like is dispersed in a wide range, and the absorption performance can be improved.

One pair of side slits 46 are respectively formed outside in the widthwise direction more significantly than the central slit 45. The side slit 46 has a longitudinally elongated shape extending along the longitudinal direction L, and is formed in the central crotch region S32. The side slit 46 is formed in the absorber 40 along the longitudinal direction L so that the absorber 40 curves in a convex manner in an outer direction OUT, namely, so that the absorber 40 curves in a convex manner which is opposite to the central slit 45.

Figure 9:
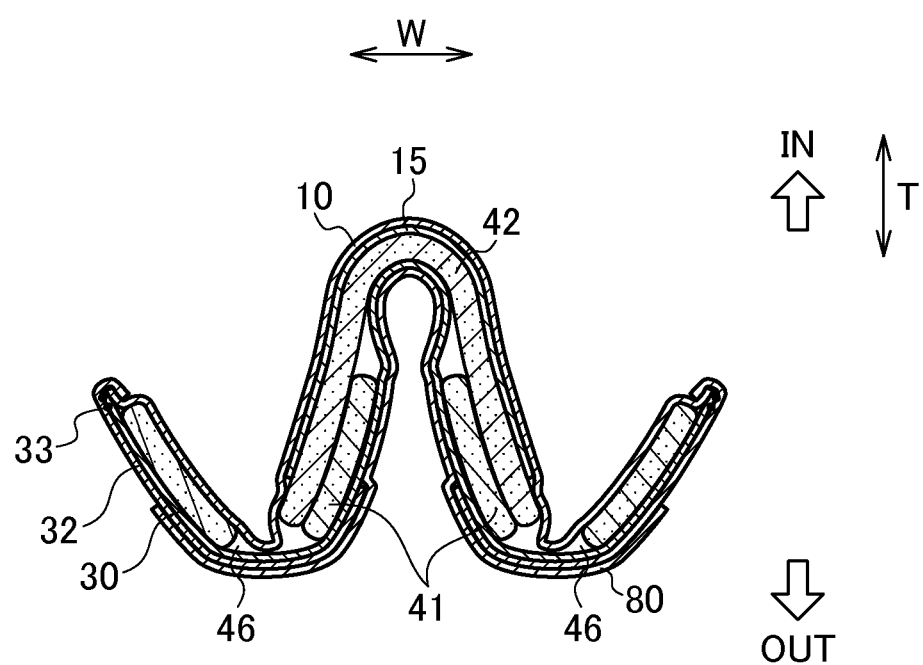
FIG. 9 is a cross-sectional view along the X1-X'1 line that schematically illustrates the wearing state of the disposable diaper according to at least one embodiment.

Next, a deformation aspect of the absorber will be described. FIG. 9 is a cross-sectional view (with reference to the X1-X'1 line of FIG. 2) that schematically illustrates the wearing state of the disposable diaper 1. As illustrated in FIG. 9, when the disposable diaper 1 is worn, the crotch region S3 of the absorber comes up against the crotch of the wearer. Due to the legs and the like of the wearer, force is applied on the absorber inwardly in the widthwise direction. The absorber 40 is curved in the inner direction IN and the outer direction OUT such that the side slits 46 and the central slit 45 are reference points. The cross-sectional shape of the disposable diaper 1 along the widthwise direction W is deformed in a wavelike manner, the central crotch region S32 of the crotch region S3 of the absorber 40 enters a regularly folded state.

The absorber is thus folded, whereby even in the case where an area of the absorber is increased so as to ensure an absorption performance, the absorber 40 in the crotch region S3 is appropriately folded to enable the absorber 40 and an excretion portion to come into intimate contact with each other. For example, as in the embodiment, even if the rear end of the absorber is disposed in the crotch region, and the length in the longitudinal direction of the absorber is comparatively small, the absorption performance is enhanced, and the leakage of bodily liquid can be restrained.

The top surface of the absorber 40, which becomes convex in the inner direction IN due to the central slit 45, comes into contact with the crotch of the wearer. The portion where the convex portion, caused by the central slit 45, is formed is configured from only the second absorbent layer 42, and is comparatively thinner. On the other hand, the first absorbent layer 41 and the second absorbent layer 42 overlap between the convex portion caused by the central slit and the convex portion caused by the side slits. This overlap portion is comparatively thicker and has high rigid. The high rigid portion between the central slit and the side slits makes it possible to support the convex portion caused by the central slit, and makes it possible to enhance the stability of the convex shape caused by the central unit.

When the wearer closes both legs, with respect to the cross-sectional shape of the disposable diaper 1, the absorber is folded over at the central slit and the side slits and is compactly disposed below the crotch of the wearer in a state of close mutual contact. Therefore, the absorption performance can be ensured while a sense of discomfort in the vicinity of the crotch portion is restrained.

At such a time, the convex portion formed by the central slit 45 is positioned so as to be in contact with the crotch of the wearer. On the other hand, the convex portion formed by the side slits 46 is convex toward the non-skin contact surface, and is positioned so as not to be in contact with the excretion opening of the wearer.

Because the absorber is in close contact at the crotch of the wearer, leakage of the bodily fluid can be prevented even in a case where urine slowly is excreted, which would run along the skin.

In the folded state, a concavity expanding in the longitudinal direction is formed at the curving unit in the portion of the absorber separated from the skin, and therefore the bodily fluid can be spread outward in the longitudinal direction and side leakage can be prevented.

Further, since a side curving unit forms a concavity portion, excretions is prone to easily get into the concavity portion, and a direct contact between the wearer's skin and the excretions can be restrained.

A convex portion formed by the central curving unit is small in thickness and high in height. Therefore, a sectional shape when the disposable diaper 1 is worn and the absorber 40 is deformed is a tapered shape narrowing from a non-skin contact surface side to a skin contact surface side. A convex portion formed by the central curving unit is prone to be easily inserted into a narrow gap of the crotch portion, and is also prone to easily come into intimate contact with the excretion opening. Since the urine opening and the absorber come into intimate contact with each other, the excreted urine can be speedily absorbed. Further, the absorber is prone to be easily included in the gap of the wearer's crotch portion, and a feeling of discomfort is hardly felt. Also, folding is carried out so that the thickness of the absorber is small at a portion which is close to the skin of the wearer's crotch portion, and the thickness is large at a portion which is distant from the skin, and therefore, fitting can be obtained without a sense of discomfort.

Next, a detailed description of a structure of the first absorbent layer 41 and the second absorbent layer 42 will be given. The first absorbent layer 41 is smaller in length in the widthwise direction from the front crotch region S31 to the central crotch region S32, and is smaller in length in the widthwise direction from the rear crotch region S33 to the central crotch region S32. In the first absorbent layer 41, a concavity portion 41N which is recessed inside in the widthwise direction from the front crotch region S31 to the central crotch region S32 is formed. The concavity portion 41N is positioned more forward than the side slit 46, and functions as a deformation restraining portion.

Since the concavity portion 41N is formed more forward than the side slit 46, a deformation exerted by the side slit 46 can be hardly transmitted to the front waistline region S1. Therefore, at the front side more significantly than the concavity portion 41N, a deformation of the absorber 40 in a convex shape is restrained, and the absorber 40 can be disposed along the wearer's skin.

The second absorbent layer 42 is formed in the shape of a substantial hourglass. The second absorbent layer has: a narrow part 42N which is positioned at a central portion in a longitudinal direction and has a predetermined width in a widthwise direction W; a front wide part 42FL which is positioned at a front side of the narrow part 42N and is large in width than the narrow part; and a rear wide part 42RL which is positioned at a rear side of the narrow part 42N and is large in width than the narrow part. A side end of the narrow part 42N, a side end of the front wide part 42FL, and a side end of the rear wide part 42RL are connected to each other by way of a curve, and the second absorbent layer 42 has an hour glass-type planar shape.

The first absorbent layer 41 and the second absorbent layer 42 are formed as one part by being pressed along the thickness direction T. Note that the first absorbent layer 41 and the second absorbent layer 42 may also be formed as one part by an adhesive and thermal fusion bonding. Furthermore, in the absorber 40, the first absorbent layer 41 is positioned at the non-skin contact surface side and the second absorbent layer 42 is positioned at the skin contact surface side, but the second absorbent layer 42 may be positioned at the non-skin contact surface side and the first absorbent layer 41 may be positioned at the skin contact surface side.

In the widthwise direction, an outside end of the narrow part 42N and an inside end of the side slit 46 are coincident with each other. According to such a structure, a difference in rigidity of the absorber 40 is formed at an end in the widthwise direction of the side slit 46, and the absorber can be stably bent while the side slit 46 is defined as a start point.

Further, as shown in FIG. 2, in the widthwise direction, an end of the auxiliary sheet 15 is positioned inside more significantly than the slide slit. Rigidity is different depending on a region in which the auxiliary sheet 15 is disposed and a region in which the auxiliary sheet 15 is not disposed (the region outside in the widthwise direction more significantly than the end in the widthwise direction of the auxiliary sheet 15). The difference in rigidity exerted by the presence or absence of the auxiliary sheet is provided, whereby curving can be easily made while a side curving unit which is composed of the side slit 46 is defined as a start point.

Also, the end in the widthwise direction of the rear wide part 42RL extends from the inside of the widthwise direction of the slide slit to the outside in the widthwise direction at the rear side more significantly than the side slit. The end in the widthwise direction of the rear wide part functions as a deformation restraining portion 42P.

The deformation restraining portion 42P is disposed more rearward than the slide slit. The deformation restraining portion 42P is disposed so as to extend from the inside of the widthwise direction to the outside in the widthwise direction as it goes from the narrow part 42N of the second absorbent layer 42 to the rear side. In a region which is more forward than the deformation restraining portion 42P, only the first absorbent layer 41 is disposed, whereas in a region more rearward than the deformation restraining portion 42P, the first absorbent layer 41 and the second absorbent layer overlaps with each other, and a difference in rigidity of the absorber arises at the deformation restraining portion. Therefore, deformation at the front side more significantly than the deformation restraining portion 42P is hardly transmitted to the rear side.

The deformation restraining portions are provided forward and rearward of the side slit 46, whereby the absorber is disposed in the crotch region while it is deformed, whereas transmission of the deformation to the rear waistline region and the front waistline region can be restrained. Further, even in the case where the front waistline region S1 and the rear waistline region S2 of the absorber are deformed, since the deformation is hardly transmitted to the crotch region, the absorber 40 can be stably folded in a convex manner in the crotch region S3.

(3) Modification Example

Next, the disposal diapers according to a modification example 1 and modification example 2 are explained with reference to drawings. Note that the same symbols are used to denote portions similar to those of the first embodiment, and the differences between the embodiments are mainly explained below.

Figure 10:
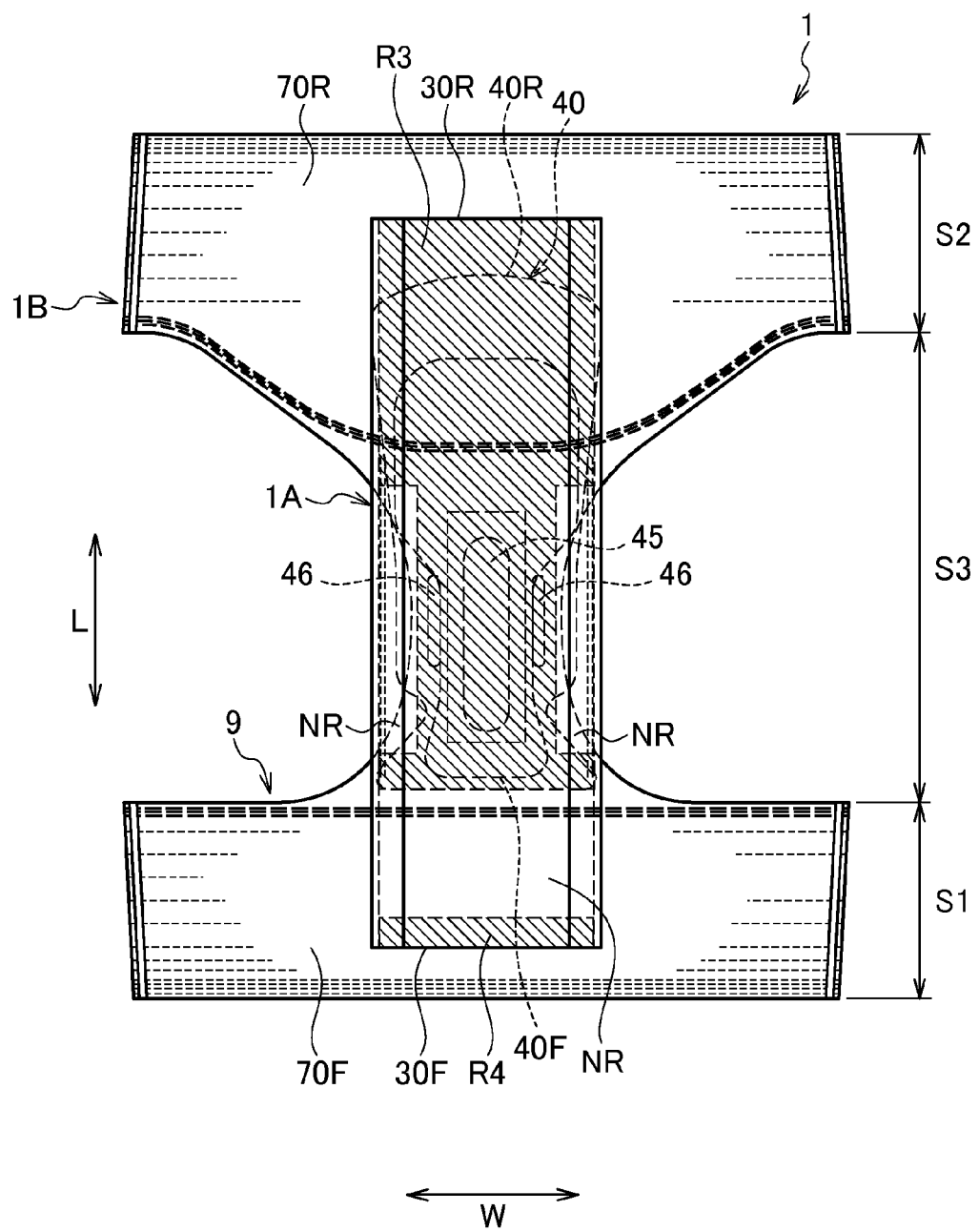
FIG. 10 is an exploded plan view of a disposable diaper according to modification example 1.

FIG. 10 is a plan view of a disposable diaper according to Modification Example 1. The disposable diaper according to Modification Example 1 is a disposable diaper in which a front end 40F of an absorber 40 is disposed in a crotch region S3, and a rear end 40R of the absorber 40 is disposed in a rear waistline region S2.

Also, an absorber backsheet 30 extends to the outside in a longitudinal direction more significantly than the absorber 40. A front end 30F of the absorber backsheet 30 is disposed in the front waistline region S1, and a rear end 30R of the absorber backsheet 30 is disposed in the rear waistline region S2. The front end 40F of the absorber 40 of the disposable diaper according to Modification Example 1 is disposed in the crotch region S3, and is small in length at the front end of the absorber in comparison with the absorber of the embodiment, and thus, there is an apprehension that a leakage arises at an abdominal side, in particular, of a crotch portion.

However, since a liquid-impermeable absorber backsheet extends more forward than the absorber, even in the case where a large amount of bodily liquid is thereby discharged and then the bodily liquid disperses forward while exceeding the front end 40F of the absorber, the leakage of the bodily liquid to the outside of the disposable diaper while exceeding an exterior body 1B can be restrained.

On the other hand, the rear waistline region is a region in which bodily liquid is prone to be easily guided in the case of a laydown posture. Since the rear end of the absorber is disposed in the rear waistline region, even in the case where bodily liquid flows in the rear waistline region along the skin at the laydown posture, the bodily liquid can be absorbed, and the leakage can be restrained.

Also, an absorbent main body 1A and the exterior body 1B are partially bonded with each other by a hot melt type adhesive. The disposable diaper according to Modification Example 1 has: a third adhesive region which is positioned between the rear end of the absorber backsheet and the front end of the absorber; and a fourth adhesive region which is positioned in the vicinity of the front end of the absorber backsheet.

Between the third adhesive region R3 and the fourth adhesive region R4 in a longitudinal direction, at a front side more significantly than the front end of the absorber, there is provided a non-adhesive region NR in which the absorbent main body 1A and the exterior body 1B are not bonded with each other. In the front waistline region, there exists a region in which no absorber is disposed and no adhesive is applied. By providing the region in which the absorber and the adhesive do not exist, the ventilation properly is improved, and the wearing comfort can be improved more remarkably. In addition, outside in the widthwise direction of the third adhesive region R3 in the crotch region S3 as well, there is provided a non-adhesive region NR in which the absorbent main body 1A and the exterior body 1B are not bonded with each other. The non-adhesive region is thus provided, whereby it is difficult for the exterior body 1B to inhibit a deformation of the absorber by a side slit. Further, even in the case where the crotch width of the absorbent main body 1A is reduced by the deformation of the absorber, the exterior body 1B can be disposed so as to cover the wearer's skin, and an uneasy sense of a leakage of bodily liquid can be reduced.

Figure 11:
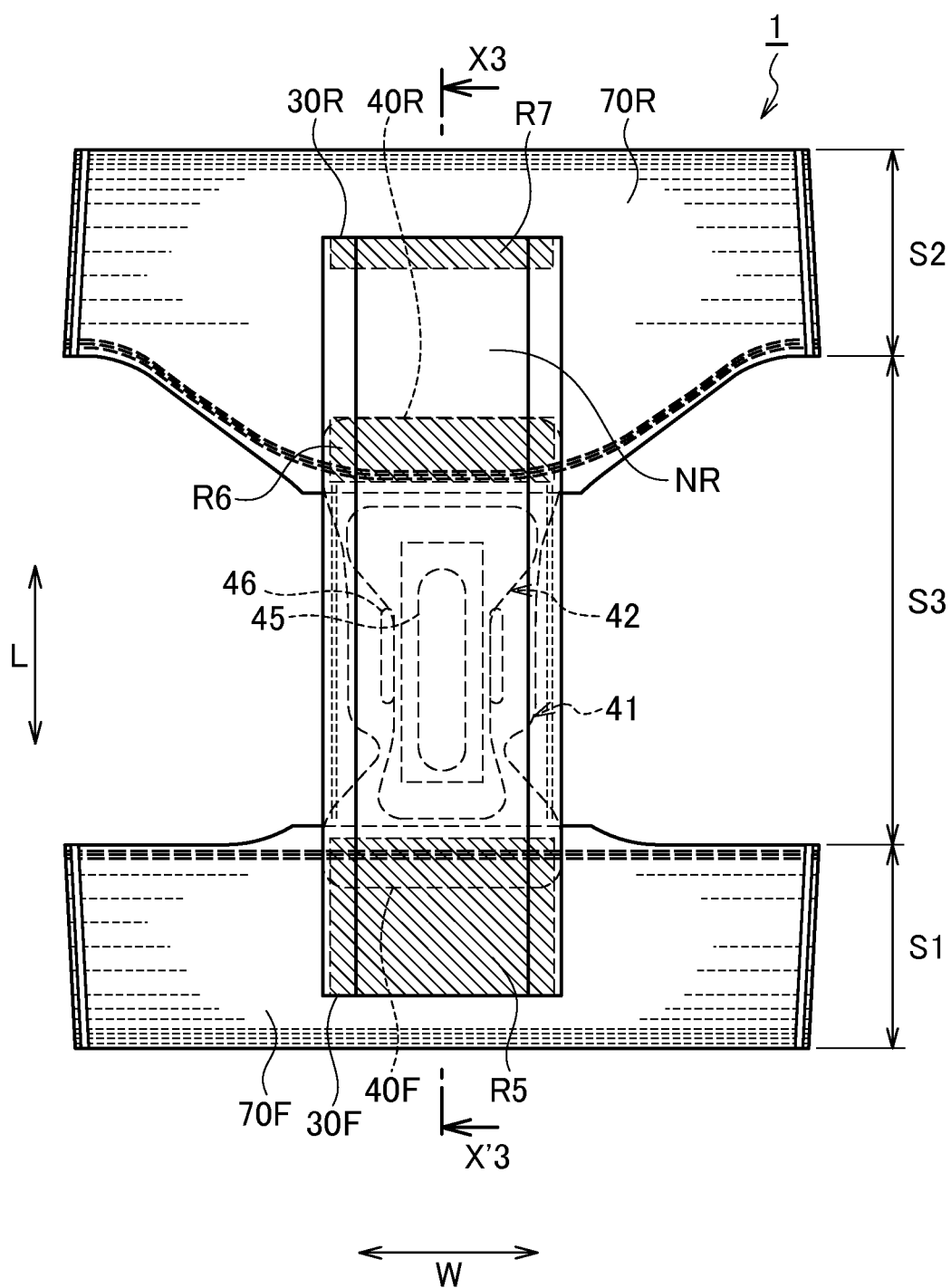
FIG. 11 is an exploded plan view of a disposable diaper according to modification example 2.
Figure 12:
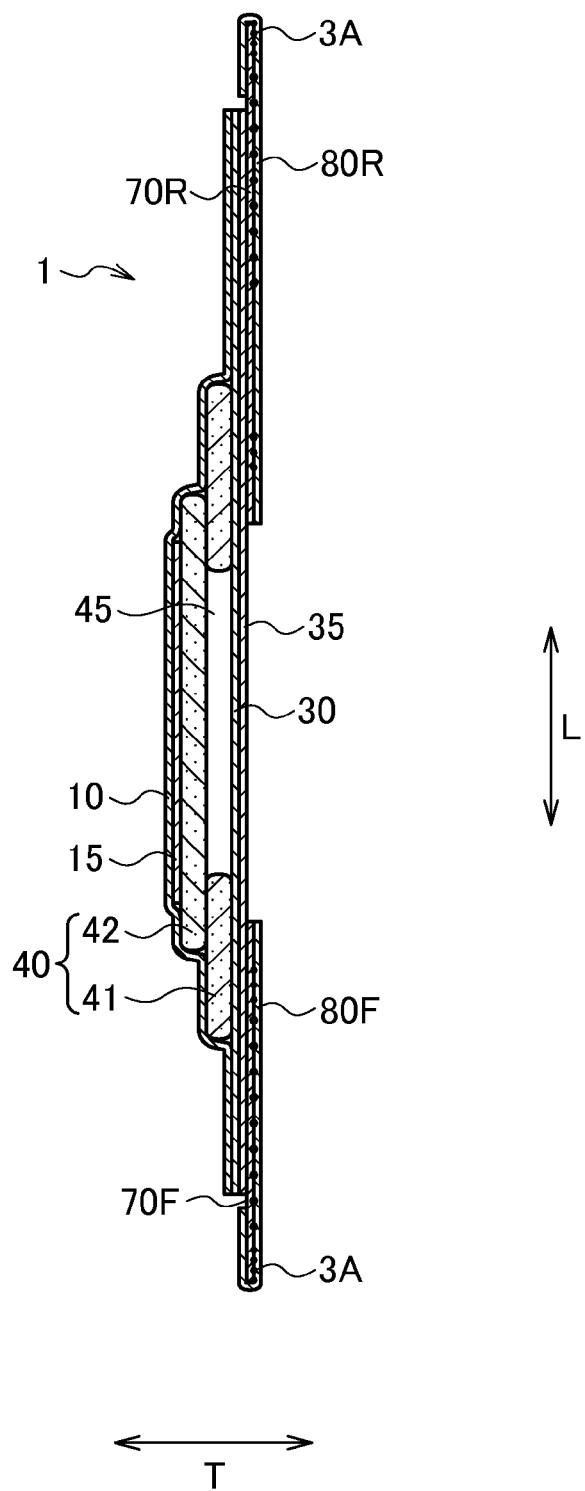
FIG. 12 is a crosswise cross-sectional view in the longitudinal direction of the disposable diaper along the X3-X'3 line shown in FIG. 11.

FIG. 11 is a plan view of a disposable diaper according to Modification Example 2. FIG. 12 is a sectional view in a longitudinal direction of the disposable diaper taken along the line X'3-X3 shown in FIG. 11. An exterior backsheet according to Modification Example 2 has: a foreside exterior backsheet 80F which is bonded with the foreside exterior topsheet 70F; and a rear-side exterior backsheet 80R which is bonded with the foreside exterior topsheet 70F. The exterior backsheet is disposed to be spaced in the longitudinal direction, whereby an area of a sheet material constituting the exterior backsheet can be reduced, and costs can be reduced.

A nonwoven sheet 35 is provided at a non-skin contact side of the absorber backsheet 30. The foreside exterior topsheet 70F and the rear-side exterior topsheet 70R are provided at the non-skin contact side of the nonwoven sheet 35. The nonwoven sheet 35 is provided, whereby, in a mode in which the exterior topsheet and the exterior backsheet are spaced from each other in the longitudinal direction, exposure of the absorber backsheet 30 of the absorbent main body 1A to the outside can be prevented.

The rear end 40R of the absorber 40 is disposed in a crotch region S3, and the front end 40F of the absorber 40 is disposed in a front waistline region S1. The rear-side exterior topsheet 70R and the rear-side exterior backsheet 80R extend more rearward than the rear end 40R of the absorber 40.

The disposable diaper according to Modification Example 2 is a disposable diaper in which the absorbent main body 1A and the exterior body 1B are bonded with each other, in planar view, in: a fifth adhesive region R5 which is positioned between the front end 30F of the absorber backsheet 30 and the front end 40F of the absorber 40; a sixth adhesive region R6 which is positioned in the vicinity of a rear end of the absorber; and a seventh adhesive region R7 which is positioned in the vicinity of a rear end of the absorber backsheet. At a rear side more significantly than the rear end 40R of the absorber 40, there is provided a non-adhesive region NR in which the absorbent main body 1A and the exterior body 1B are not bonded with each other.

The fifth adhesive region R5 is disposed 10 mm or more forward than the rear ends of the foreside exterior topsheet 70F and the foreside exterior backsheet 80F. The sixth adhesive region R6 is disposed 10 mm or more rearward than the front ends of the rear-side exterior topsheet 70R and the rear-side exterior backsheet 80R. Thus, the rear ends of the foreside exterior topsheet 70F and the foreside exterior backsheet 80F (or the front ends of the rear-side exterior topsheet 70R and the rear-side exterior backsheet 80R) and the fifth adhesive region (or the sixth adhesive region) are disposed to be spaced from each other by 10 mm or more, whereby, in case that the exterior body 1B turns up, adhering of the adhesive to cloth can be prevented.

(4) Other Embodiments

As described above, although several embodiments of the present invention are disclosed, the description and drawings forming part of this disclosure are not intended to limit the present invention. From this disclosure, a variety of substitutive embodiments, examples, and operational techniques would become apparent to one ordinarily skilled in the art.

For example, while, in the foregoing embodiments, a pants-type disposable diaper was described by way of example, the present invention is not limited thereto, and may be applied to an open-type disposable diaper, an incontinence pad, and a sanitary napkin or the like.

In so far as an open-type disposable diaper is concerned, for example, in a rear waistline region, an engagingly fitting member such as a fastening tape is provided, and in a front waistline region, a target portion by which the engagingly fitting member is to be hooked is provided.

Therefore, the waistline region and the rear waistline region come into intimate contact with the wearer's waistline. At least one of the front end and the rear end of the absorber is disposed in the crotch region, thereby improving the ventilation property in the front waistline region and the rear waistline region that come into intimate contact with the wearer's waistline by way of the engagingly fitting member or the like, and the wearing comfort can be improved.

In addition, the absorbent article may be provided with a central curving unit and a side curving unit, may be provided with at least one of them, or alternatively, may not be provided with the central curving unit and the side curving unit.

Further, although the central curving units and the side curving units of the embodiment are composed of slits formed in the absorber, the structure of the central curving units and the side curving units are not limitative to the slits. The central curving units and the side curving units may be composed of an elastic member which expands and contracts in the longitudinal direction, may be composed of a compression unit by which the absorber is compressed in the thickness direction, or alternatively, may be composed of a low basis weight region which is structured to be lower than the basis weight of the periphery in the absorber. Furthermore, a slit is formed in the absorber, and an elastic member to expand and contract in the longitudinal direction so as to overlap with the slit is provided, whereby a central curving unit and a side curving unit may be composed of the slit and the elastic member.

In aforementioned embodiments, the absorber 40 has a bi-layered structure of the first absorbent layer 41 and the second absorbent layer 42, but the absorber 40 of the worn article according to further embodiments may be configured from a single layer or may be configured from three or more layers As described above, needless to say, the present invention includes various embodiments and the like not described here. Accordingly, the scope of the present invention is defined only by the appended claims in view of the above description.

The entire contents of Japanese Patent Application No. 2012-098248 (filed on Apr. 23, 2012) are incorporated in the present specification by reference.

INDUSTRIAL APPLICABILITY

According to the characteristic provided by the present invention, it is possible to provide an absorbent article which improves a ventilation property while preventing a leakage of bodily liquid, and which is capable of improving a wearing comfort of a wearer.

REFERENCE SIGNS LIST

1 . . . Disposable diaper (absorbent article)
1A . . . Absorbent main body
1B . . . Exterior body
3 . . . Waist gathers
3A . . . Waist elastic member
4, 4' . . . Front waistline side edge
5 . . . Leg gathers
5F . . . Front leg-holes elastic member
5R . . . Rear leg-holes elastic member
6, 6' . . . Rear waistline side edge
8 . . . waistline opening unit 9 . . . leg opening unit
9C . . . Inclination part
10 . . . Topsheet
11 . . . joint unit
15 . . . Auxiliary sheet
30 . . . Absorber backside sheet
30F . . . Front end
30R . . . Rear end
32 . . . Leakage preventing side sheet
33 . . . Leakage preventing elastic member
35 . . . Nonwoven sheet
40 . . . Absorber
40F . . . Front end
40R . . . Rear end
41 . . . First absorbent layer
41N . . . Concavity portion
42 . . . Second absorbent layer
42FL . . . Front wide part
42N . . . narrow part
42RL . . . Rear wide part
42P . . . Deformation restraining portion
45 . . . Central slit
46 . . . side slit
70F . . . Foreside exterior topsheet
70R . . . Rear-side exterior topsheet
80 . . . Exterior backsheet
80F . . . Foreside exterior backsheet
80R . . . Rear-side exterior backsheet
S1 . . . Front waistline region
S2 . . . Rear waistline region
S3 . . . Crotch region
S31 . . . Front crotch region
S32 . . . Central crotch region
S33 . . . Rear crotch region
L . . . longitudinal direction
IN . . . Inner direction
OUT . . . Outer direction
T . . . Thickness direction
W . . . Widthwise direction
NR . . . Non-adhesive region
R1 . . . First adhesive region
R2 . . . Second adhesive region
R3 . . . Third adhesive region
R4 . . . Fourth adhesive region
R5 . . . Fifth adhesive region
R6 . . . Sixth adhesive region
R7 . . . Seventh adhesive region

The invention claimed is:

1. An absorbent article having:
a longitudinal direction extending to a body front side and a body rear side of a wearer;
a widthwise direction perpendicular to the longitudinal direction;
an inner direction for facing a wearer;
an outer direction which is opposite to the inner direction;
a crotch region which is adapted to be in contact with a crotch of the wearer;
a front waistline region which is disposed forward of the crotch region, and is adapted to be in contact with a waistline of the wearer;
a rear waistline region which is disposed rearward of the crotch region, and is adapted to be in contact with the waistline of the wearer,
an absorber which is disposed at least in the crotch region; and
a liquid-impermeable sheet which is positioned at the outer direction side of the absorber, wherein
a rear end of the absorber is disposed in the crotch region,
a front end of the absorber is disposed in the front waistline region,
a rear end of the liquid-impermeable sheet is disposed outboard of the crotch region in the longitudinal direction,
the liquid-impermeable sheet has a ventilation property,
an exterior sheet disposed on a surface of a non-skin contact side of the absorbent article is provided at the outer direction side of the liquid-impermeable sheet,
the absorbent article further having:
an adhesive region in which an adhesive bonds the liquid-impermeable sheet and the exterior sheet with each other is applied; and
a non-adhesive region in which the adhesive is not applied, and
the non-adhesive region is positioned posteriorly of the rear end of the absorber and extends continuously from the crotch region to the rear waistline region.

2. The absorbent article according to claim 1, wherein
a leg opening unit disposed along a leg-line of the wearer is formed in the crotch region, and
a waistline elastic member to expand and contract in the widthwise direction is provided in the front waistline region and the rear waistline region.

3. The absorbent article according to claim 1, wherein a central curving unit that allows the absorber to curve in the inner direction in a convex shape is formed at a center of the crotch region in a widthwise direction.

4. The absorbent article according to claim 3, wherein one pair of side curving units that allow the absorber to curve in the outer direction in a convex shape are formed outboard the central curving unit in the crotch region in a widthwise direction.

5. An absorbent article having:
a longitudinal direction extending to a body front side and a body rear side of a wearer;
a widthwise direction perpendicular to the longitudinal direction;
an inner direction for facing a wearer;
an outer direction which is opposite to the inner direction,
a crotch region which is adapted to be in contact with a crotch of the wearer;
a front waistline region which is disposed forward of the crotch region, and is adapted to be in contact with a waistline of the wearer;
a rear waistline region which is disposed rearward of the crotch region, and is adapted to be in contact with the waistline of the wearer,
an absorber which is disposed at least in the crotch region; and
a liquid-impermeable sheet which is positioned at the outer direction side of the absorber, wherein
a front end of the absorber is disposed in the crotch region,
a rear end of the absorber is disposed in the rear waistline region,
the front end of the liquid-impermeable sheet is disposed outboard of the crotch region in the longitudinal direction,
the liquid-impermeable sheet has a ventilation property,
an exterior sheet disposed on a surface of a non-skin contact side of the absorbent article is provided at the outer direction side of the liquid-impermeable sheet,
the absorbent article further having:
an adhesive region in which an adhesive bonds the liquid-impermeable sheet and the exterior sheet with each other is applied; and a non-adhesive region in which the adhesive is not applied, and the non-adhesive region is positioned anteriorly of the front end of the absorber and extends continuously from the crotch region to the front waistline region.

6. The absorbent article according to claim 5, wherein
a leg opening unit disposed along a leg-line of the wearer is formed in the crotch region, and
a waistline elastic member to expand and contract in the widthwise direction is provided in the front waistline region and the rear waistline region.

7. The absorbent article according to claim 5, wherein a central curving unit that allows the absorber to curve in the inner direction in a convex shape is formed at a center of the crotch region in a widthwise direction.

8. The absorbent article according to claim 7, wherein one pair of side curving units that allow the absorber to curve in the outer direction in a convex shape are formed outboard the central curving unit in the crotch region in a widthwise direction.

* * * * *